United States Patent [19]

Averill et al.

[11] Patent Number: 4,798,610
[45] Date of Patent: Jan. 17, 1989

[54] PROSTHETIC IMPLANT DEVICE

[75] Inventors: Robert G. Averill, Ringwood; Alex Khowaylo, Allendale, both of N.J.

[73] Assignee: Osteonics Corp., Allendale, N.J.

[21] Appl. No.: 427,010

[22] Filed: Sep. 29, 1982

[51] Int. Cl.[4] ................................................ A61F 2/34
[52] U.S. Cl. .................................................... 623/22
[58] Field of Search .......................... 3/1.912, 1.913; 128/92 C, 92 CA; 403/114–125

[56] References Cited

U.S. PATENT DOCUMENTS

| 2,841,428 | 7/1958 | Moskovitz | 403/135 |
| 4,231,673 | 11/1980 | Satoh et al. | 403/125 |
| 4,241,463 | 12/1980 | Khovaylo | 128/92 CA X |

FOREIGN PATENT DOCUMENTS

| 0053794 | 6/1982 | European Pat. Off. | 623/22 |
| 2301810 | 7/1973 | Fed. Rep. of Germany | 3/1.912 |
| 2069338 | 8/1981 | United Kingdom | 3/1.912 |

Primary Examiner—Richard J. Apley
Assistant Examiner—David J. Isabella
Attorney, Agent, or Firm—Samuelson & Jacob

[57] ABSTRACT

A prosthetic implant device for use in replacing the ball end of a biological joint, the replacement including a spherical head for insertion into a natural socket, an insert in the head, a ball-shaped member captured in the insert and having a neck and a stem for mounting the ball-shaped member on the end of the biological member on which the ball is being replaced, and a radially-expansible ring for capturing the ball-shaped member within the insert the ring having a downwardly and inwardly sloping outer wall and seated in a recess in the insert, the recess having upper and lower end walls for defining upper and lower limits of axial movement of the ring within the recess to permit selective removal of the ball-shaped member from the insert and to prevent inadvertent disengagement of the ball-shaped member from the insert.

4 Claims, 1 Drawing Sheet

PROSTHETIC IMPLANT DEVICE

The present invention relates generally to femoral hip prostheses, and, more particularly, to a femoral head and neck prosthesis for implant and interaction with the natural bone structure of the pelvic acetabulum.

The pelvis in the human body contains two hip bones, one on each side of the body, each containing an acetabulum or hip socket for receiving and forming a seat for the femoral head, or ball, of the femur or thigh bone. The femoral head is connected to the thigh bone by a neck which is angularly disposed relative to the axis of the femur and relative to the vertical axis of the body. Thus, any load applied by the body through the hip and femoral neck to the thigh bone and leg and any impacts, such as in walking, jumping and the like, applied by the leg and thigh bone through the femoral neck and hip to the body are transmitted angularly through the femoral neck. This angular transmission of the load and forces through the femoral neck results in high stresses and high sheer loads applied to the femoral neck. These high stresses, abnormally applied, can cause fracture of the femoral neck.

Various attempts heretofore have been made to provide femoral head and necks for surgical implant in the natural acetabulum enabling replacement of the natural head and neck which have been damaged or broken. Thus, in U.S. Pat. Nos. 3,813,699 and 3,863,273 there are shown and described femoral heads and necks for such surgical implant and replacement for damaged or broken natural heads or necks. In both such devices, an outer spherical metal cup, having an inner plastic insert, is provided for implanting in the acetabulum or hip socket. The inner plastic insert has a socket into which a metal sphere, having a neck and a stem for connection to the thigh bone, is pivotaly received.

While the devices of such patents provide replacements for surgical implant when the natural femoral head or neck are broken or damaged, such devices can become displaced after implant. Thus, the outer spherical metal cup may become displaced from the hip socket, the inner plastic insert may become displaced from the outer cup, or the metal sphere may become displaced from the plastic insert. Such displacement may arise when the leg or body is abnormally twisted, much in the same manner as might result in dislocation in the normal hip in a person having a propensity for hip dislocation. The difficulty in such patented devices when dislocation occurs is in the relocation of the implant once dislocation occurs, without resort to new surgery. While the parts dislocated might be identified in the customary manner, such as by x-ray, such devices do not lend themselves to relocation reliably without surgery. This is because in attempting to realign or relocate the dislocated elements with each other, such as by twisting or pulling in the conventional manner, other parts in the device, at the time aligned and properly located, can be misaligned and even disengaged from one another, compounding rather than correcting the original dislocation. Such compounding can require surgical correction.

In U.S. Pat. No. 4,241,463, many of the difficulties heretofore encountered in providing an implantable replacement for the femoral head and neck for use with the natural acetabulum or hip joint are overcome. While still employing an outer spherical cup, an inner insert and a metal sphere having a neck and a stem for connection to the thigh bone, the cup, insert and sphere are interconnected and implanted in the natural acetabulum in an attempt to preclude disengagement of the component parts, one from the other.

The femoral head and neck prosthetic implant of U.S. Pat. No. 4,241,463 includes an outer spherical cup, an inner insert and a metal sphere having a neck and a stem for connection to the thigh bone and for insertion into a socket in the inner insert. The outer cup may be of metal and the inner insert may be of plastic. The cup and insert may be interconnected by a mating protuberance and groove and the plastic insert extends outwardly and along the edge of the metal cup. The outer cup and the inner insert may be of one piece, such as of impact and abrasive-resistant ceramic having a low coefficient of friction. The lower or entry end of the inner insert socket is tapered and slopes downwardly and inwardly toward the socket open end. A plastic split ring, having a sloping outer wall corresponding with the slope on the wall of the insert and a curved inner wall for seating on the spherical surface of the metal sphere are provided between the metal sphere and the insert so that the metal sphere may be inserted into the insert and, once in place, will be captured for pivotal movement in the insert.

However, it has been found that under certain circumstances, albeit unusual circumstances, such as during manipulation to relocate a previously dislocated device, a combination of forces applied to the prosthetic implant device of U.S. Pat. No. 4,241,463 can result in the disengagement of the component parts of the device, one from the other. Thus, under the influence of such an unusual combination of forces, it is possible that the plastic split ring can be peeled from between the metal sphere and the insert; that is, the split ring can be tilted or skewed so that the split ring can pass between the metal sphere and the insert, a portion at a time, until the complete split ring is released from the insert, thereby inadvertently releasing the metal sphere from the insert.

It is an object of the present invention to provide a femoral head and neck prosthetic, implant having all of the advantages of the device described in the aforesaid U.S. Pat. No. 4,241,463, and including an improvement for precluding relative disengagement of the component parts even under the most unusual circumstances and conditions encountered during the service life of the device.

Another object of the invention is to provide an improvement of the type described above, and which constitutes only a minor change in the overall structure of a device of known effectiveness so as to have available all of the benefits of the earlier device plus those of the improvement.

Still another object of the invention is to provide an improvement of the type described above, and in which the minor structural changes preserve much of the original device for interchangeability, thereby enabling economy of manufacture and use.

Yet another object of the invention is to provide an improvement of the type described and in which a relatively small change in structure attains a marked improvement in performance.

A further object of the invention is to provide an improvement of the type described and which enables ease in the selective disassembly of the assembled component parts while increasing resistance to inadvertent disengagement of the component parts.

A still further object of the invention is to provide an improvement of the type described and which enables continued use through known techniques developed for the use of earlier devices while attaining improved performance over a longer service life.

The above objects, as well as still further objects and advantages, are attained by the present invention which may be described briefly as an improvement in an implantable prosthetic joint for use in replacement of the ball end of a biological joint, the prosthetic joint having a spherical head for insertion into and seating in the natural socket of the joint, a bearing in the spherical head, the bearing including an inner spherical dome having an entrance end and an outwardly extending recess located axially between the entrance end and the inner spherical dome, the recess extending circumferentially around the bearing and having a laterally outwardly extending upper end wall and an outer wall extending downwardly from the upper end wall and sloping downwardly and inwardly toward the entrance end, a ball-shaped member for being seated in the inner spherical dome of the bearing and a radially-expansible ring placed between the bearing and a portion of the ball-shaped member when the ball-shaped member is seated in the inner spherical dome for capturing the ball-shaped member in the bearing, the ring having an upper end wall confronting the upper end wall of the recess, an outer wall sloping downwardly and inwardly for contacting the outer wall of the recess and an arcuate wall for contacting the ball-shaped member when the downward ball-shaped member is urged downwardly against the ring by forces tending to disengage the ball-shaped member from the inner spherical dome, the length of the outer sloping wall of the ring being substantially shorter than the length of the outer sloping wall of the recess for permitting the ring to slide upwardly toward an upper position wherein the ring will expand in the recess in response to contact with the ball-shaped member as the ball-shaped member is inserted through the entrance end into the bearing toward the inner spherical dome, until the ball-shaped member can pass through the ring to permit the ring to slide downwardly in the recess away from the recess upper end wall and between the outer sloping wall of the recess and the ball-shaped member, beneath the ball-shaped member, upon the application of downward forces to the ball-shaped member, the improvement wherein: the recess includes a laterally inwardly extending lower end wall confronting the upper end wall of the recess and spaced axially downwardly from the recess upper end wall a distance great enough to permit movement of the ring in axial directions between the upper position and a lower position wherein contraction of the ring beneath the ball-shaped member by contact with the outer wall of the recess will capture the ball-shaped member in the bearing, between the inner spherical dome and the arcuate wall of the ring, and to permit the ring to be pushed selectively by a disengagement tool upwardly toward the upper position in the recess so that the ring will be expanded outwardly sufficiently for the ball-shaped member to be withdrawn through the ring and from the bearing; and the ring includes a lower end wall confronting the lower end wall of the recess such that movement of the ring downwardly beyond the recess lower end wall and consequent disengagement of the ring from the recess will be precluded by contact between at least portions of the ring lower end wall and the recess lower end wall, thereby preventing inadvertent disengagement of the ball-shaped member from the spherical head.

The invention will be more fully understood, while still further objects and advantages will become apparent, in the following detailed description of a preferred embodiment illustrated in the accompanying drawing, in which.

Figures 1, 2, 3, 4, 5:
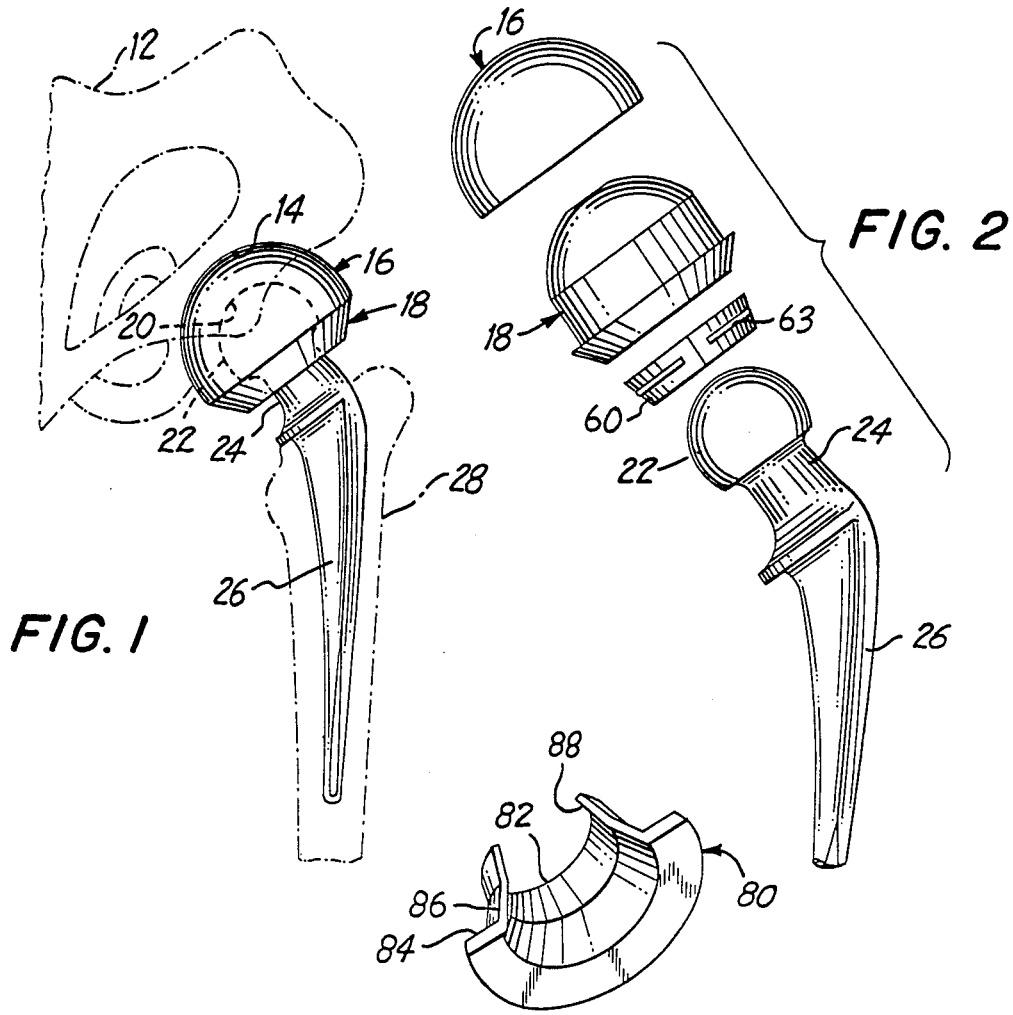
FIG. 1 is a pictorial view, in full and phantom lines, and taken from the front, showing in phantom line, the natural pelvis, acetabulum, and thigh bone and, in full line, the implant device of the instant invention.
FIG. 2 is an enlarged exploded view, of the implant device of the instant invention showing the parts in their relative assembly position.
FIG. 3 is an enlarged elevational view, partly in section, showing the outer spherical cup, the inner plastic insert, the metal sphere and neck, as the metal sphere is being inserted into the outer spherical cup and plastic insert assembly.
FIG. 4 is an enlarged pictorial view, similar to FIG. 3 but showing the metal sphere, outer cup and plastic insert assembled.
FIG. 5 is a perspective view of a disengagement tool used for releasing the metal sphere from the plastic insert.

Referring now to the drawing and especially to FIGS. 1 and 2 thereof, the pelvis, generally designated 12, has an acetabulum or hip socket 14. The spherical cup, generally designated 16, has a bearing shown in the form of an insert, generally designated 18, seated in sphere 16 and in turn having a socket 20 for receiving sphere 22, having a neck 24 and stem 26 for implant in thigh bone 28.

The materials of spherical cup 16, insert 18, sphere 22, neck 24 and stem 26 may be of any material compatible with body tissues of the patient in which the implant device of the instant invention is to be implanted and of sufficient strength to withstand forces which will be encountered. Cup 16 and insert 18 may be of one piece and of impact, wear and abrasion resistant ceramic and neck 24 and stem 26 might be of metal. Preferably, spherical cup 16, sphere 22, neck 24 and stem 26 are of a metal material. Materials, such as cobalt chrome molybdenum alloy ASTM F-75 and stainless steel ASTM F-139-71 are especially suited for this purpose. Insert 18 preferably is made from a low-friction material having sufficient strength, abrasion resistance and rigidity to accommodate the forces which will be applied. Ultra-high molecular weight polyethylene is a material suitable for this purpose.

Turning to FIGS. 3 and 4, spherical cup 16 has an outer spherical surface 30 and an inner spherical dome 32. Spherical dome 32 terminates in a cylindrical skirt 34, extending downwardly from the dome to the open end of the spherical cup 16. So as to complement spherical dome 32 and cylindrical skirt 34, insert 18 has an outer spherical dome 40, and a downwardly extending cylindrical skirt 42. Insert 18 is received within cup 16 and is secured therein by a plurality of discrete barbs 44 unitary with cup 16 and projecting inwardly from cylindrical skirt 34 at circumferentially spaced locations into complementary cylindrical skirt 42 of the insert to anchor insert 18 within cup 16 in the desired joined relationship. At its lower end, below skirt 42, the outer wall of plastic insert 18 extends outwardly at 46, along the bottom wall of spherical cup 16 and then slopes downwardly and inwardly, at 48 to the open end of insert 18.

The inner surface of plastic insert 18 has an inner spherical dome 50 to receive spherical head 22. Preferably, the center of spherical dome 50 is offset by a small distance upwardly relative to the center of outer spherical surface 30. Below dome 50, the inner surface of insert 18 includes an outwardly extending recess 52 having an upper end wall 54 extending laterally outwardly to an outer wall 56 which slopes downwardly and inwardly to a lower end wall 58 which extends laterally inwardly, confronts upper end wall 54 and is spaced axially downwardly from upper end wall 54. Lower end wall 58 terminates at an inner peripheral edge 59 adjacent the open end of insert 18.

A ring 60, preferably constructed of the same plastic material as that of the insert 18, has a split 62, rendering the ring 60 radially expansible and contractible. Biasing means in the form of a split wire spring 63 is placed around the outer perimeter of ring 60 to supplement the memory of the material of ring 60 and bias the ring toward the radially contracted configuration. Ring 60 includes an upper end wall 64, a downwardly and inwardly sloping outer wall 66 of the same slope as outer wall 56 of recess 52 of insert 18 for mating engagement therewith, a lower end wall 68 and an inner arcuate wall 70 for mating with the lower portion of sphere 22 when ring 60 is located in the lower position thereof, shown in FIG. 4, beneath the spherical head 22. An intermediate portion 72 of ring 60 projects radially inwardly to intercept the sphere 22 as the sphere is inserted axially into insert 18, and through ring 60, so that ring 60 will be raised axially upwardly to the upper position, shown in FIG. 3, where the ring 60 is expanded radially, in response to contact between the sphere 22 and projecting portion 72, to permit sphere 22 to pass through ring 60 and be seated in dome 50. A tapered lower portion 74 facilitates such insertion.

The femoral hip prosthesis device of the instant invention is assembled by first joining plastic insert 18 with spherical cup 16, with spherical dome 40 of insert 18 in contact with inner spherical dome 32 of cup 16 and barbs 44 embedded in skirt 42 to secure insert 18 in place within cup 16. Sloping wall 48 of insert 18 slopes downwardly and inwardly below the end wall of metal spherical cup 16, preventing contact of the cup end wall with bone and other body tissue, as will be later described.

With insert 18 secured in cup 16, split ring 60 is inserted through the open end of plastic insert 18 and the end of sphere 22 is inserted into the open end of insert 18. As the dome of sphere 22 enters the cavity in insert 18 and contacts projecting portion 72 of ring 60, ring 60 is raised, wall 64 of ring 60 engages inwardly extending wall 52 of insert 18 and ring 60 expands, allowing sphere 22 to enter the cavity of insert 18 and permitting the spherical surface of sphere 22 to be brought into contact with spherical dome 50 in insert 18. With the dome of sphere 22 in contact with spherical dome 50 of insert 18, the radially inward biasing of the split ring causes split ring 60 to contract and slide downwardly along sloping wall 64, capturing sphere 22 in insert 18.

The axial spacing between the upper end wall 54 of recess 52 in insert 28 and lower end wall 58, coupled with the slope of outer wall 56 enables axial movement of ring 60 between the upper and lower positions illustrated in FIGS. 3 and 4. In the upper position of ring 60, the confronting upper end walls 54 and 64 engage one another and the upper end wall 64 of ring 60 will slide radially along the upper end wall 54 of insert 18, as the sphere 22 is inserted, such sliding movement being facilitated by the material of the insert 18 and the ring 60 and by the radial orientation of the end walls 54 and 64, which end walls extend generally perpendicular to the axial direction. In the lower position of ring 60, the slope of outer wall 56 of recess 52 and the corresponding slope of outer wall 66 of ring 60 assure that the ring 60 is contracted to capture sphere 22 in place in insert 18. Should any forces be applied which may tend to tilt or skew the ring 60, and consequently tend to peel the ring 60 from between the insert 18 and the sphere 22, at least a portion of lower end wall 68 of ring 60 will contact a corresponding portion of lower end wall 58 of the recess 52 to preclude any movement of the ring 60 downwardly beyond the lower end wall 58 of recess 52, thereby preventing inadvertent disengagement of the sphere 22 from the insert 18. The radial orientation of confronting lower end walls 58 and 68, generally perpendicular to the axial direction, assures that ring 60 is locked positively in place within recess 52 and sphere 22 is captured securely within the insert 18.

In effecting the surgical implant of the device, cup 16 and insert 18, with split ring 60 therein, might be assembled and positioned in the acetabulum or hip socket 14. Sphere 22, neck 24 and stem 26 might then be fixed to the thigh bone by implanting stem 26 in the thigh bone 28. Next, sphere 22 might be inserted into the insert 18, which is in cup 16 located in hip socket 14, and captured within insert 18 by split ring 60. The prosthetic device of the invention might also be fully assembled, stem 26 inserted and attached to thigh bone 28 and the outer spherical surface 30 of cup 16 might then be inserted into the acetabulum or hip socket 14.

Once assembled, spherical cup 16, plastic insert 18 and sphere 22, with neck 24 and stem 26, function as a unit. That is, sphere 22 cannot be removed or disengaged from insert 18, and insert 18, with sphere 22 in place, cannot be separated or displaced from cup 16. Thus, any unusual force which might be applied to the prosthetic device of the instant invention, once the device is surgically implanted, and cause displacement or disengagement, will result in the dislocation of the prosthetic hip joint of the invention as a unit much in the same manner as would occur at the joint in a natural hip. In other words, the device of the instant invention will remain as a unit and will be displaced as a unit from the acetabulum or hip socket 14 at cup 16. The hip prosthesis of the instant invention, should it become displaced or dislocated, can be restored to its proper position by manipulating the leg or thigh bone in the same manner as in the relocation of a dislocated natural hip. Forces applied to the device during such manipulation to relocate or realign a previously dislocated device will not result in the disengagement of component parts of the device, one from the other, and the device will remain assembled so as to function as a unit, even after dislocation of the device. The sloping wall 48 of the plastic insert, extending over and covering the end of the spherical cup 16, guides the prosthetic device back into place and tends to prevent damage to body tissue, in the same manner as described in connection with the device of Pat. No. 4,241,463, when the prosthetic device of the instant invention is being manipulated, in conventional manner, to relocate a displaced hip joint.

Once the device of the instant invention has been assembled and surgically implanted, disassembly of the device should not be necessary. However, should it become necessary or desirable to disassemble the unit, a disengagement tool may be used to accomplish ready disassembly. In FIG. 5, a disengagement tool 80 is seen to include a cylindrical segment projection 82 interconnected to a radial flange 84 by a tapered portion 86, the cylindrical segment construction providing a longitudinal opening 88 in the tool. As seen in FIG. 4, when ring 60 is in the lower position with lower end wall 68 contacting lower end wall 58 of recess 52, the lower end wall 68 extends laterally inwardly beyond the inner peripheral edge 59 of lower end wall 58. Thus, tool 80 may be slipped laterally over neck 24, which will pass through opening 88 of tool 80, and projection 82 may be inserted through the open end of insert 18, and between the neck 24 and insert 18, facilitated by tapered surface 90 at the open end, to be placed against the inwardly projecting portion of lower end wall 68, as seen in phantom in FIG. 4. An axially upward force applied to flange 84 will be transmitted to ring 60, causing axially upward movement of ring 60 to the upper position thereof and release of the sphere 22 for selective withdrawal through ring 60 from insert 18.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. In an implantable prosthetic joint for use in replacement of the ball end of a biological joint, said prosthetic joint having a spherical head for insertion into and seating in the natural socket of the joint, a bearing in said spherical head, said bearing including an inner spherical dome having an entrance end and an outwardly extending recess located axially between the entrance end and the inner spherical dome, the recess extending circumferentially around the bearing and having a laterally outwardly extending upper end wall and an outer wall extending downwardly from said upper end wall and sloping downwardly and inwardly toward the entrance end, a ball-shaped member for being seated in said inner spherical dome of said bearing, the relative dimensions of the ball-shaped member and the entrance end enabling the ball-shaped member to be inserted into and selectively released from the bearing through the entrance end, and a radially-expansible ring placed between the bearing and a portion of the ball-shaped member when the ball-shaped member is seated in the inner spherical dome for capturing the ball-shaped member in the bearing, the ring having an upper end wall confronting the upper end wall of the recess, an outer wall sloping downwardly and inwardly for contacting said outer wall of said recess and an arcuate wall for contacting said ball-shaped member when the ball-shaped member is urged downwardly against the ring by downward forces tending to disengage the ball-shaped member from the inner spherical dome, the length of the outer sloping wall of said ring being substantially shorter than the length of the outer sloping wall of said recess for permitting said ring to slide upwardly toward an upper position wherein the ring will expand in said recess in response to contact with the ball-shaped member as the ball-shaped member is inserted through the entrance end into the bearing toward the inner spherical dome, until said ball-shaped member can pass through said ring to permit said ring to slide downwardly in said recess away from said recess upper end wall and between said outer sloping wall of said recess and said ball-shaped member, beneath the ball-shaped member, upon the application of downward forces to said ball-shaped member, the improvement wherein:

the recess includes a laterally inwardly extending lower end wall confronting the upper end wall of the recess and spaced axially downwardly from the recess upper end wall a distance great enough to permit movement of the ring independent of the ball-shaped member in axial directions between said upper position and a lower position wherein contraction of the ring beneath the ball-shaped member by contact with the outer wall of the recess will capture the ball-shaped member in the bearing, between the inner spherical dome and the arcuate wall of the ring, and to permit said ring to be pushed selectively by a disengagement tool upwardly toward said upper position in said recess independent of the ball-shaped member so that said ring will be expanded outwardly sufficiently for said ball-shaped member to be withdrawn through said ring and said entrance end to be released selectively from said bearing; and the ring includes a lower end wall confronting the lower end wall of the recess such that movement of the ring downwardly beyond the recess lower end wall and consequent disengagement of the ring from the recess will be precluded by contact between at least portions of the ring lower end wall and the recess lower end wall, thereby preventing inadvertent disengagement of the ball-shaped member from the spherical head.

2. The invention of claim 1 wherein:

the lower end wall of the recess extends laterally inwardly to an inner peripheral edge; and the lower end wall of the ring extends laterally inwardly beyond the inner peripheral edge of the recess lower end wall such that the disengagement tool will engage the lower end wall of the ring for said selective pushing of the ring.

3. The invention of claim 2 wherein:

the inner peripheral edge of the lower end wall extends circumferentially essentially entirely around the recess; and the lower end wall of the ring extends laterally inwardly beyond the inner peripheral edge of the recess lower end wall essentially entirely around the ring.

4. The invention of claim 1, 2 or 3 wherein the lower end wall of the ring extends in a radial direction, generally perpendicular to the axial direction.

* * * * *